(12) United States Patent
Furnish

(10) Patent No.: US 7,672,713 B2
(45) Date of Patent: Mar. 2, 2010

(54) MULTI-CHANNEL CATHETER TIP

(75) Inventor: Simon Furnish, New York, NY (US)

(73) Assignee: InfraReDx, Inc., Burlington, MA (US)

( * ) Notice: Subject to any disclaimer, the term of this patent is extended or adjusted under 35 U.S.C. 154(b) by 1309 days.

(21) Appl. No.: 10/175,479

(22) Filed: Jun. 19, 2002

(65) Prior Publication Data

US 2003/0236453 A1 Dec. 25, 2003

(51) Int. Cl.
*A61B 6/00* (2006.01)
(52) U.S. Cl. .................. 600/476; 600/473; 600/477; 600/478; 600/407
(58) Field of Classification Search .......... 600/439, 600/585, 433–435, 309–344, 473–480, 407; 607/122; 606/1–19
See application file for complete search history.

(56) References Cited

U.S. PATENT DOCUMENTS

| | | | | |
|---|---|---|---|---|
| 3,543,744 A | * | 12/1970 | Lepar ...................... 600/435 |
| 4,570,638 A | | 2/1986 | Stoddart et al. ............ 128/665 |
| 4,740,047 A | | 4/1988 | Abe et al. ................ 350/96.15 |
| 4,896,941 A | | 1/1990 | Hayashi et al. .......... 350/96.25 |
| 4,921,326 A | | 5/1990 | Wild et al. ............... 350/96.26 |
| 5,014,204 A | | 5/1991 | Kamimura et al. .......... 364/449 |
| 5,169,395 A | | 12/1992 | Narciso, Jr. ................. 606/7 |
| 5,190,538 A | | 3/1993 | Hussein et al. ............. 606/17 |
| 5,195,968 A | * | 3/1993 | Lundquist et al. ........ 604/95.04 |
| 5,197,470 A | | 3/1993 | Helfer et al. .............. 128/634 |
| 5,242,438 A | | 9/1993 | Saadatmanesh et al. ....... 606/15 |
| 5,253,312 A | | 10/1993 | Payne et al. ................ 385/31 |
| 5,292,320 A | | 3/1994 | Brown et al. ............... 606/15 |
| 5,318,024 A | | 6/1994 | Kittrell et al. ............. 128/634 |
| 5,343,543 A | | 8/1994 | Novak, Jr. et al. ........... 385/31 |
| 5,353,790 A | | 10/1994 | Jacques et al. ............. 128/633 |
| 5,354,294 A | | 10/1994 | Chou ...................... 606/16 |
| 5,427,107 A | * | 6/1995 | Milo et al. ................. 600/463 |
| 5,496,309 A | | 3/1996 | Saadat et al. ............... 606/15 |
| 5,681,280 A | * | 10/1997 | Rusk et al. .............. 604/96.01 |
| 5,713,364 A | | 2/1998 | DeBaryshe et al. ......... 128/664 |
| 5,878,178 A | | 3/1999 | Wach ..................... 385/55 |

(Continued)

FOREIGN PATENT DOCUMENTS

DE  EP 0 947 221  * 6/1999

(Continued)

OTHER PUBLICATIONS

Patent abstracts of Japan vol. 1999, No. 14, Dec. 22, 1999 $JP 11 253562 (Terumo Corp), Sep. 21, 1999.

(Continued)

*Primary Examiner*—Long V Le
*Assistant Examiner*—Sanjay Cattungal
(74) *Attorney, Agent, or Firm*—Rothwell, Figg, Ernst & Manbeck, P.C.

(57) ABSTRACT

A tip assembly for a catheter includes a housing having a recess that receives an optical bench. The optical bench accommodates adjacent fibers, one of which is in optical communication with a first beam re-director. The first beam re-director is oriented to cause a beam incident thereon to travel in a direction away from the optical bench. An engaging structure coupled to the optical bench provides torque coupling between the housing and an end of a torque cable extending axially along the catheter.

31 Claims, 12 Drawing Sheets

U.S. PATENT DOCUMENTS

| | | | | |
|---|---|---|---|---|
| 5,901,261 | A | 5/1999 | Wach | 385/38 |
| 5,953,477 | A | 9/1999 | Wach et al. | 385/115 |
| 5,993,467 | A * | 11/1999 | Yoon | 606/147 |
| 5,995,875 | A * | 11/1999 | Blewett et al. | 607/98 |
| 6,055,451 | A | 4/2000 | Bambot et al. | 600/476 |
| 6,091,984 | A | 7/2000 | Perelman et al. | 600/476 |
| 6,134,003 | A * | 10/2000 | Tearney et al. | 356/479 |
| 6,144,791 | A | 11/2000 | Wach et al. | 385/123 |
| 6,263,224 | B1 * | 7/2001 | West | 600/373 |
| 6,327,493 | B1 | 12/2001 | Ozawa et al. | 600/476 |
| 6,343,227 | B1 | 1/2002 | Crowley | 600/407 |
| 6,589,233 | B1 | 7/2003 | Maki | |
| 6,654,630 | B2 * | 11/2003 | Zuluaga et al. | 600/476 |
| 6,701,181 | B2 * | 3/2004 | Tang et al. | 600/478 |
| 7,050,692 | B2 * | 5/2006 | Harlan et al. | 385/136 |
| 2002/0183623 | A1 * | 12/2002 | Tang et al. | 600/476 |
| 2003/0028114 | A1 * | 2/2003 | Casscells et al. | 600/474 |

FOREIGN PATENT DOCUMENTS

| | | |
|---|---|---|
| EP | 0 947 221 | 10/1999 |
| EP | 0 947 221 A | 10/1999 |
| EP | 1 075 821 | 2/2001 |
| EP | 1 075 821 A | 2/2001 |
| FR | 2 681 522 | 3/1993 |
| FR | 2 681 522 A | 3/1993 |
| FR | 2681522 | 3/1993 |
| JP | 11-253562 | 12/1998 |
| JP | 2001046394 | 2/2001 |
| WO | WO 01/11409 | 2/2001 |
| WO | WO02/096478 | 12/2002 |

OTHER PUBLICATIONS

Barber et al., "Ultrasonic Duplex Echo-Doppler Scanner," *IEEE Transactions on Biomedical Engineering*, vol. BME-21, No. 2, pp. 109-113 (Mar. 1974).

Bow et al., "Cardiac Imaging with a Real-Time Ultrasonic Scanner of a Rotating Transducer Design," *Proceedings of The British Medical Ultrasound Society*, p. 645 (Aug. 1978).

"Coronary-Artery Bypass Surgery," *The Lancet*, pp. 264-265 (Feb. 4, 1978).

Hisanaga et al., "High Speed Rotating Scanner for Transesophageal Cross-Sectional Echocardiography," *The American Journal of Cardiology*, vol. 46, pp. 837-842 (Nov. 1980).

Lancée et al., "Construction of a circular ultrasonic array with miniature elements for cardiac application," Thorax Center, Department of Echocardiography and Central Research Workshop, Erasmus University, Rotterdam, The Netherlands, pp. 49-53 (undated).

Martin et al., "An Ultrasonic Catheter Tip Instrument for Measuring Volume Blood Flow," Departments of Anesthesiology & Bioengineering, University of Washington, Seattle, Washington, pp. 13-17 (undated).

Martin et al., "Ultrasonic Catheter Tip Instrument for Measurement of Vessel, Cross-Sectional Area," 27th ACEMB, Marriott Hotel, Philadelphia, Pennsylvania, p. 186 (Oct. 6-10, 1974).

Martin and Watkins, "An Ultrasonic Catheter for Intravascular Measurement of Blood Flow: Technical Details," *IEEE Transactions on Sonics and Ultrasonics*, vol. SU-27, No. 6, pp. 277-286 (Nov. 1980).

Pérez et al., "Applicability of Ultrasonic Tissue Characterization for Longitudinal Assessment and Differentiation of Calcification and Fibrosis in Cardiomyopathy," *American College of Cardiology*, vol. 4, No. 1, pp. 88-93 (Jul. 1984).

Tomoike et al., "Continuous measurement of coronary artery diameter in situ," *American Physiological Society*, pp. H73-H79 (undated).

Van Orden et al., "A technique for monitoring blood flow changes with miniaturized Doppler flow probes," *American Physiological Society*, pp. H1005-H1009 (undated).

Ycas and Barnes, "An Ultrasonic Drill for Cleaning Blood Vessels," Department of Electrical Engineering, University of Colorado, Boulder, Colorado, pp. 165-167 (undated).

* cited by examiner

MULTI-CHANNEL CATHETER TIP

FIELD OF INVENTION

This invention relates to catheters, and in particular, to catheters that accommodate more than one optical fiber.

BACKGROUND

Certain lipid-filled cavities that form within the wall of a blood vessel are known as "vulnerable plaques." These plaques, when ruptured, can cause massive clotting in the vessel. The resultant clot can interfere with blood flow to the brain, resulting in a stroke, or with blood flow to the coronary vessels, resulting in a heart attack.

To locate vulnerable plaques, one inserts a catheter through the lumen of the vessel. The catheter includes a delivery fiber for carrying infrared light that will ultimately illuminate a spot on the vessel wall and a collection fiber for carrying infrared light scattered from a collection area on the vessel wall.

The distal tip of such a catheter includes a stationary transparent jacket enclosing a rotatable housing that holds the delivery and collection fibers. In addition to these fibers, the housing encloses two mirrors: one to bend a beam exiting the delivery fiber so that it illuminates the wall; and another to gather scattered light from the wall and to direct that scattered light into the collection fiber.

A vulnerable plaque can be anywhere within the wall of the vessel. As a result, it is desirable to circumferentially scan the illuminated spot and the collection area around the vessel wall. One way to do this is to spin the multi-channel catheter about its axis. This requires providing a torque cable and coupling the housing to the torque cable.

The housing at the distal tip, which is already crowded with optical elements, must now accommodate a coupling element to enable torque transmitted by the torque cable to rotate the housing. One way to accommodate this additional element is to enlarge the housing. However, an enlarged housing at the distal tip of a catheter is undesirable because of the limited size of the blood vessels through which the catheter is intended to pass.

SUMMARY

The invention is based on the recognition that a side-by-side arrangement of fibers results in a more compact tip assembly for a catheter. Such an arrangement can readily accommodate a coupling element that enables the tip to rotate.

One aspect of the invention is a catheter tip assembly in which a recess in a housing receives an optical bench. The optical bench has a transverse dimension selected to accommodate adjacent first and second fibers. The bench holds the first fiber in optical communication with a first beam re-director. The first beam re-director is oriented to cause a beam to travel away from the optical bench. An engaging structure coupled to the optical bench provides torque coupling between the housing and an end of a torque cable extending axially along a catheter.

When measured relative to an axis of an optical catheter, a direction can have a radial component, which is perpendicular to the axis, an axial component, which is parallel to the axis, and a circumferential component, which is perpendicular to the radial component and the axial component. As used herein, the phrase "away from the optical bench" means a direction that includes a radial component. Thus, "away from the optical bench" includes directions that may also include axial or circumferential components, in addition to the radial component.

In another aspect, the invention includes a catheter having a rotatable torque cable through which first and second optical fibers extend. A distal tip assembly as described above is coupled to the torque cable.

Another aspect of the invention is a catheter tip assembly having an optical bench. A recess extending along a longitudinal axis of the optical bench has a transverse dimension selected to accommodate adjacent first and second fibers. The optical bench includes a first beam re-director in optical communication with the first fiber. The first beam re-director is oriented to cause a beam to travel away from the optical bench. An engaging structure coupled to the optical bench provides a torque coupling between the housing and an end of a torque cable extending axially along a catheter.

The invention also includes a method for receiving light by inserting a distal tip assembly into a blood vessel. The distal tip assembly encloses first and second fibers extending axially to a tip assembly. These fibers lie on a plane at the tip assembly. Light traveling on the first fiber is then directed away from the plane. Meanwhile, light incident on the plane is received into the second fiber.

The catheter tip assembly may include a second beam re-director in optical communication with the second fiber. The second beam re-director is oriented to cause a beam to travel in a direction having a second radial component. The magnitudes of the first and second radial components need not be the same, in which case beams re-directed by the first and second beam re-directors travel in different directions. In addition, a beam re-director can direct a beam in a direction having only a radial component, in which case the beam is essentially perpendicular to a plane containing the first and second fibers.

Either the first or second beam re-director can be a mirror. However, other beam re-directors, such as diffraction gratings, or prisms, are within the scope of the invention. In embodiments having both first and second beam re-directors, different types of beam re-directors can be used. For example, the first beam re-director could be a mirror while the second beam re-director is a prism.

The engaging structure can include an annular coupling mount disposed between the torque cable and the housing. The annular coupling mount has a first face coupled to the torque cable and a second face for engaging the housing.

The housing may include a proximally extending stem for inserting into an aperture in the annular coupling mount. Alternatively, the housing may include a tab extending proximally from a periphery thereof. In this case, the annular coupling mount includes a distal face having walls forming a slot for receiving the tab. Or, the annular coupling mount may include a tab extending distally from a periphery thereof, in which case the housing includes walls forming a slot for receiving the tab. In some embodiments, a hook extending proximally from the annular coupling mount and into a recess in the housing provides torque coupling.

As used herein, term "light" includes not only visible light, but also electromagnetic radiation in the ultraviolet, infrared and the near infrared bands. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The adjacent configuration of delivery and collection fibers results in a distal tip assembly having a small cross section. In addition, the adjacent configuration leaves space available for a torque coupling element within the housing. As a result, the diameter of the housing need not be enlarged to accommodate a coupling to the torque cable.

Other features and advantages of the invention will be apparent from the following detailed description, and from the claims.

DETAILED DESCRIPTION

System Overview

Figure 1:
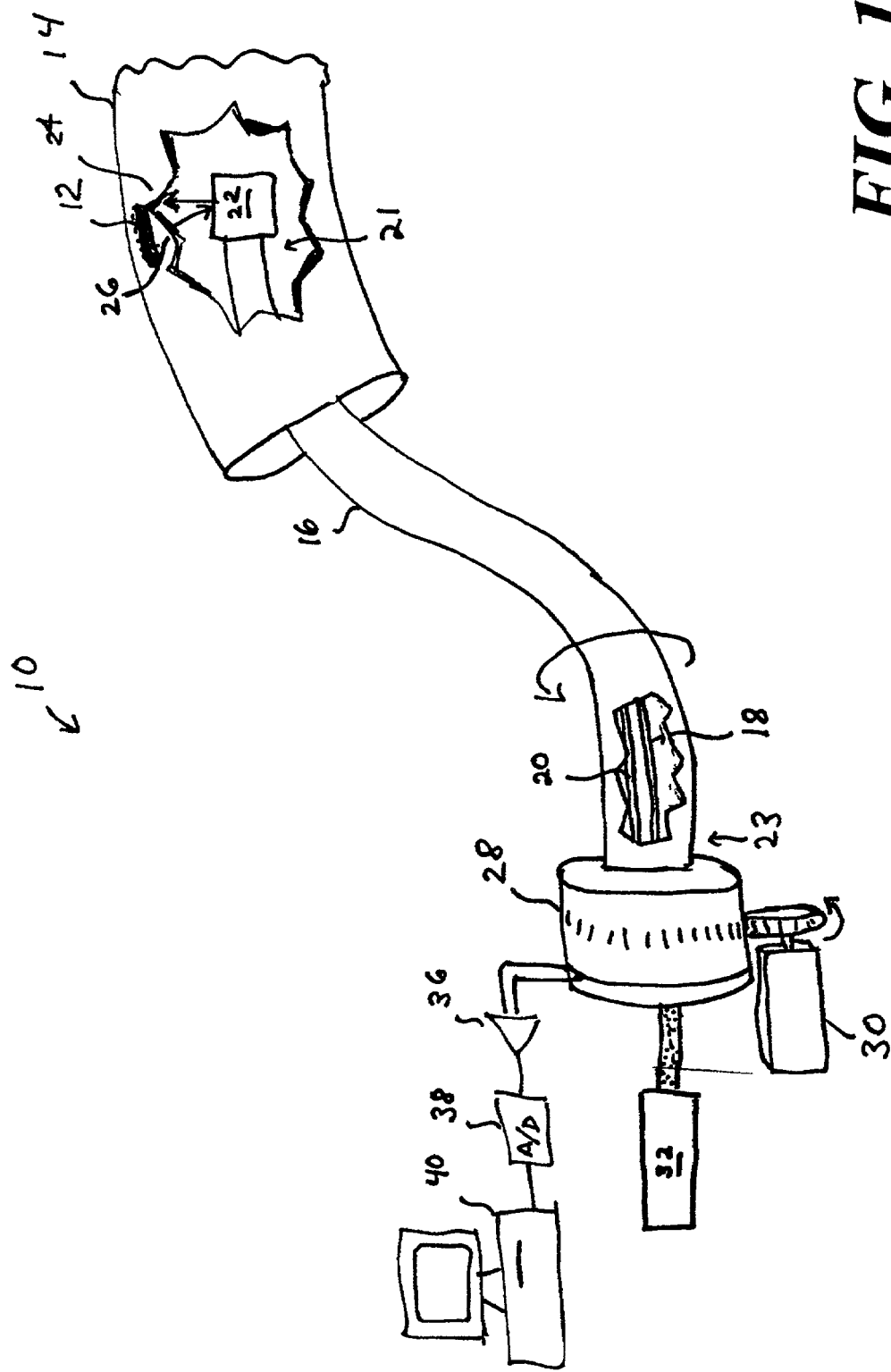
FIG. 1 is a schematic of a system for identifying vulnerable plaque in a patient.

FIG. 1 shows a diagnostic system 10 for identifying vulnerable plaque 12 in an arterial wall 14 of a patient. The diagnostic system features a catheter 16 to be inserted into a selected artery, e.g. a coronary artery, of the patient. A delivery fiber 18 and a collection fiber 20 extend between a distal end 21 and a proximal end 23 of the catheter 16.

Figure 2:
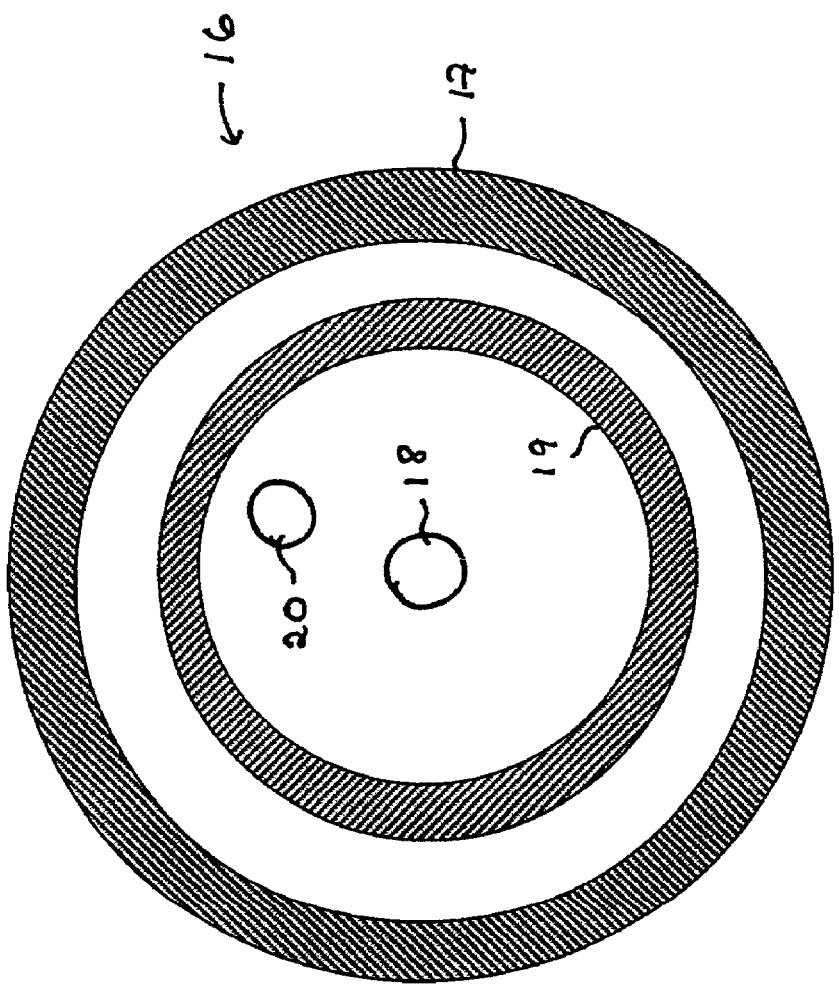
FIG. 2 is a cross-section of the catheter in FIG. 1.

As shown in FIG. 2, the catheter 16 includes a jacket 17 surrounding a rotatable torque cable 19. The delivery fiber 18 extends along the center of a torque cable 19, and the collection fiber 20 extends parallel to, but radially displaced from, the delivery fiber 18. The rotatable torque cable 19 spins at rate between approximately 1 revolution per minute and 400 revolutions per minute.

At the distal end 21 of the catheter 16, a tip assembly 22 coupled to the torque cable 19 directs light traveling axially on the delivery fiber 18 toward an illumination spot 24 on the arterial wall 14. The tip assembly 22 also collects light from a collection area 26 on the arterial wall 14 and directs that light into the collection fiber 20.

A multi-channel coupler 28 driven by a motor 30 engages the proximal end 23 of the torque cable 19. When the motor 30 spins the multi-channel coupler 28, both the coupler 28, the torque cable 19, and the tip assembly 22 spin together as a unit. This feature enables the diagnostic system 10 to circumferentially scan the arterial wall 14 with the illumination spot 24.

In addition to spinning the torque cable 19, the multi-channel coupler 28 guides light from a laser 32 (or other light source such as a light-emitting diode, a super-luminescent diode, or an arc lamp) into the delivery fiber 18 and guides light emerging from the collection fiber 20 into one or more detectors (not visible in FIG. 1).

The detectors provide an electrical signal indicative of light intensity to an amplifier 36 connected to an analog-to-digital ("A/D") converter 38. The A/D converter 38 converts this signal into digital data that can be analyzed by a processor 40 to identify the presence of a vulnerable plaque 12 hidden beneath the arterial wall 14.

Optical Bench

Figure 3:
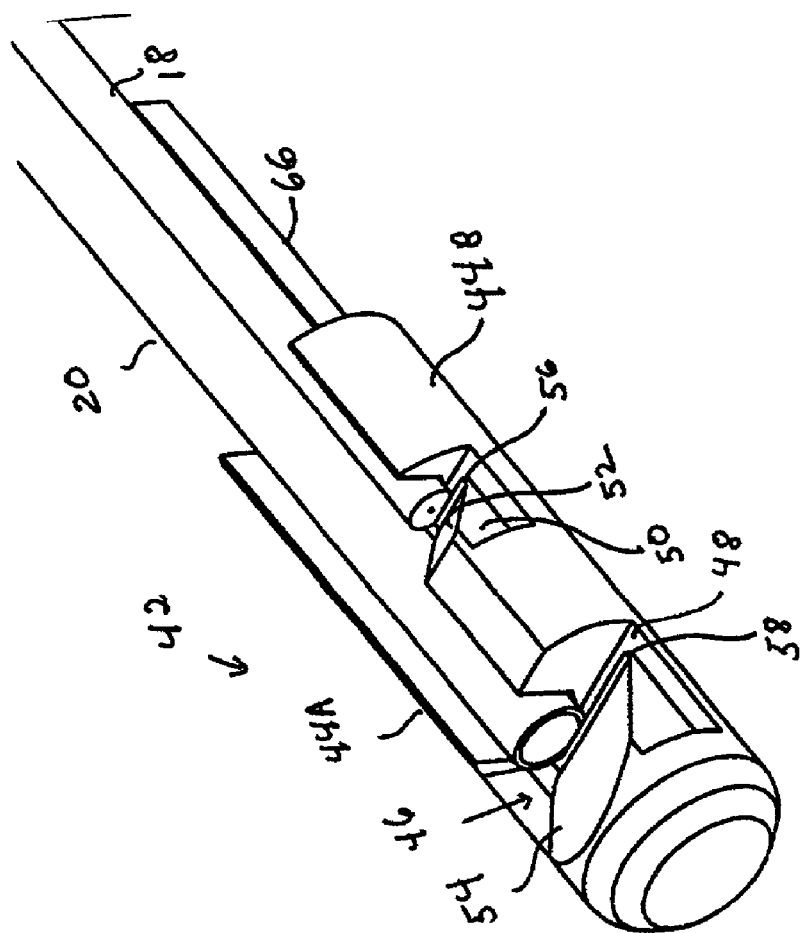
FIG. 3 is a view of an optical bench at the tip assembly of the catheter in FIG. 1.

FIG. 3 shows an optical bench 42 in which are seated the collection fiber 20 and the delivery fiber 18. The optical bench 42 is seated in a recess 46 between first and second side walls 44A-B of the distal end of a housing 62 (best seen in FIG. 5). The housing 62 is in turn coupled to the distal end of the torque cable 19. The recess 46 is just wide enough to enable the collection fiber 20 and the delivery fiber 18 to nestle adjacent to each other. A floor 48 extending between the first and second side walls 44A-B and across the recess 46 supports both the collection and delivery fibers 18, 20.

Just distal to the end of the delivery fiber 18, a portion of the optical bench 42 forms a frustum 50. The frustum 50 extends transversely only half-way across the optical bench 42, thereby enabling the collection fiber 20 to extend distally past the end of the delivery fiber 18.

The frustum 50 has an inclined surface facing the distal end of the delivery fiber 18 and a vertical surface facing the distal end of the optical bench 42. The inclined surface forms a 135 degree angle relative to the floor 48. Other angles can be selected depending on the direction in which light from the delivery fiber 18 is to be directed. A reflective material coating the inclined surface forms a beam re-director, which in this case is a delivery mirror 52. When light exits axially from the delivery fiber 18, the delivery mirror 52 intercepts that light and redirects it radially outward to the arterial wall 14. Examples of other beam re-directors include prisms and diffraction gratings.

The collection fiber 20 extends past the end of the delivery fiber 18 until it terminates at a plane that is coplanar with the vertical face of the frustum 50. Just beyond the distal end of the collection fiber 20, a portion of the optical bench 42 forms an inclined surface extending transversely across the optical bench 42 and making a 135 degree angle relative to the floor 48. A reflective material coating the inclined surface forms a collection mirror 54. This collection mirror 54 reflects light incident from the arterial wall 14 into the distal end of the collection fiber 20.

In the embodiment of FIG. 3, the fibers 18, 20 are in direct optical communication with their respective mirrors 52, 54, with no intervening optical elements. However, in some embodiments, a lens assembly is interposed between the distal end of the delivery fiber 18 and the delivery mirror 52. In other embodiments, a lens assembly is interposed between the distal end of the collection fiber 20 and the collection mirror 54. In yet other embodiments, a lens assembly is interposed between the distal end of the collection fiber 20 and the collection mirror 54 and also between the distal end of the delivery fiber 18 and the delivery mirror 52.

The lens assembly can include one or more discrete lenses. A suitable lens for use in a lens assembly is a GRIN (graduated index of refraction) lens. In addition, the lens assembly need not be composed of discrete lenses but can instead include a lens that is integral with the distal end of the fiber 18, 20. Such a lens can be made by shaping the distal end of the optical fiber 18, 20 so that it has the desired optical characteristics.

As shown in FIG. 3, the beam re-director is a separate element disposed in optical communication with a fiber 18, 20. However, the beam re-director can also be integral with the delivery fiber 18 in which case the delivery mirror 52 is rendered unnecessary. Or, the beam re-director can be integral with the collection fiber 20, in which case the collection mirror 54 is rendered unnecessary. Or the beam re-director can be integral with both the collection fiber 20 and the delivery fiber 18, in which case both the collection mirror 54 and the delivery mirror 52 are rendered unnecessary.

Figure 4:
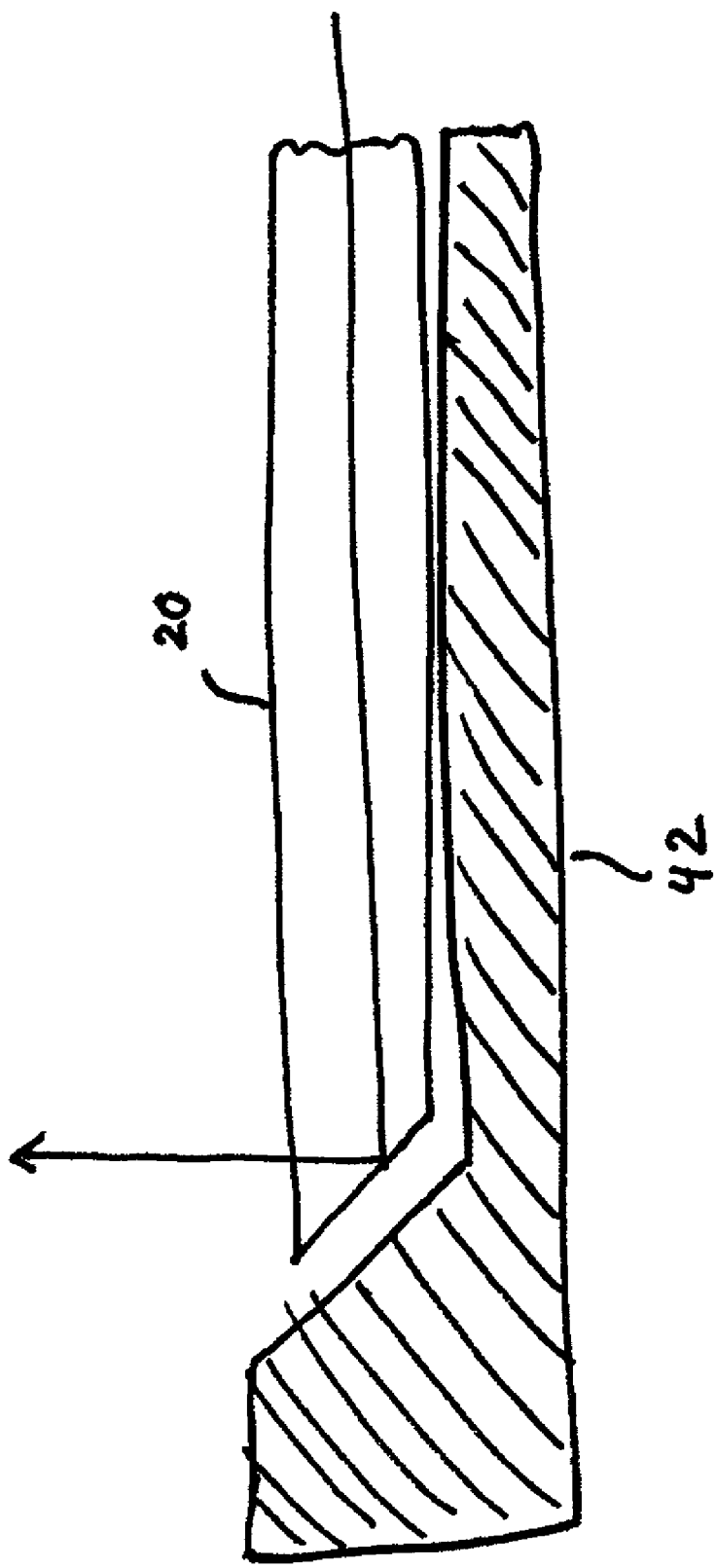
FIG. 4 is a view of an optical bench in which a fiber has a distal tip shaped to function as a beam re-director.

FIG. 4 shows one example of the various ways in which a beam re-director can be integrated into a fiber. In FIG. 4, a fiber, which in this case is the delivery fiber 18, has a distal end that has a diagonal cut forming a diagonal face. Light traveling axially along the fiber is reflected at the diagonal face and directed radially outward, toward the wall of the delivery fiber 18. By orienting the delivery fiber 18 with its diagonal face facing radially inward, this light is made to travel in a direction away from the optical bench 42. As shown in FIG. 4, the angle of the diagonal cut is on the order of forty-five degrees. However, it will be appreciated that different angles will still direct the light away from optical bench 42, but will introduce an axial component into the direction in which the light is directed.

Although FIG. 4 shows a delivery fiber 18 having a beam re-director integrated therein, it will be appreciated that a beam re-director can also be integrated into the distal end of the collection fiber 20 using the same physical principles.

In the embodiment described herein, the collection fiber 20 extends beyond the delivery fiber 18. However, this need not be the case. In some embodiments, the delivery fiber 18 extends beyond the collection fiber 20. Alternatively, the delivery fiber 18 and the collection fiber 20 can end on the same plane. This is particularly useful when the distal tip assembly is intended to recover light scattered from very nearby regions, such as when information on features of the blood, rather than the vessel wall, is sought. In this case, the frustum 50 is eliminated and the space freed by doing so is used to accommodate the additional length of delivery fiber 18. Light entering the collection fiber 20 and leaving the delivery fiber 18 can both be incident on the same beam re-director. Alternatively, light entering the collection fiber 20 and leaving the delivery fiber 18 can be incident on separate beam re-directors.

The surfaces of the delivery and collection mirrors 52, 54 can be coated with a reflective coating, such as gold, silver or aluminum. These coatings can be applied by known vapor deposition techniques. Alternatively, for certain types of plastic, a reflective coating can be electroplated onto those surfaces. Or, the plastic itself can have a reflective filler, such as gold or aluminum powder, incorporated within it.

A fiber stop 56 molded into the optical bench 42 proximal to the frustum 50 facilitates placement of the delivery fiber 18 at a desired location proximal to the delivery mirror 52. A similar fiber stop 58 molded into the optical bench 42 just proximal to the collection mirror 54 facilitates placement of the collection fiber 20 at a desired location proximal to the collection mirror 54.

The optical bench 42 is manufactured by injection molding a plastic into a mold. In addition to being simple and inexpensive, the injection molding process makes it easy to integrate the elements of the optical bench 42 into a single monolith and to fashion structures having curved surfaces. Alternatively, the optical bench can be manufactured by micro-machining plastic or metal, by lithographic methods, by etching, by silicon optical bench fabrication techniques, or by injection molding metal.

Figure 5:
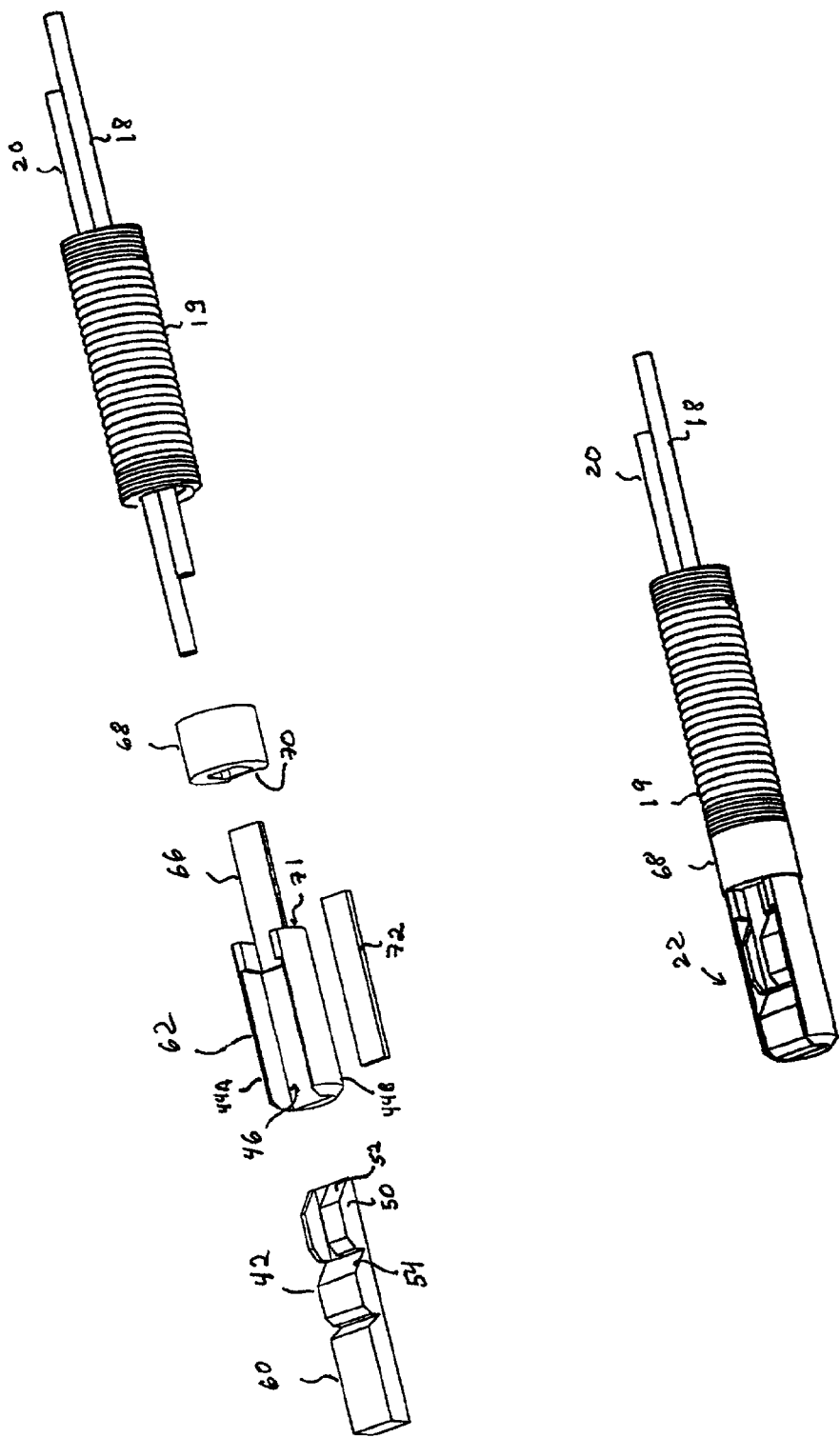
FIG. 5 is an exploded view of the tip assembly in FIG. 3.

A breakaway handle 60, shown in FIG. 5, is attached to the distal end of the optical bench 42. This breakaway handle 60 is used to insert the optical bench 42 into a housing 62 that couples to the torque cable 19, as described below.

Materials other than plastics can be used to manufacture the housing 62 and the optical bench 42. Such materials include metals, quartz or glass, ceramics, liquid crystal polymers (LCPs), polyphenylsulfone, polyethersulfone, and polyetherimide.

The floor 48 in the illustrated embodiment is integral to the housing 62. However, the floor 48 can also be made part of the optical bench 42.

As described herein, the housing 62 and the optical bench 42 are manufactured separately and later joined. However, the housing 62 and the optical bench 42 can also be manufactured together as a single unitary structure.

Coupling to Torque Cable

FIG. 5 is an exploded view of the distal tip assembly 22 showing the manner of coupling to the torque cable 19. As noted above, the distal end of the housing 62 has walls 44A-B forming an axially extending recess 46 sized and shaped to accommodate the optical bench 42. The optical bench 42, with its breakaway handle 60 still in place, is slid proximally into the recess 46 from the distal end of the housing 62. Once the optical bench 42 is seated in the recess 46, the breakaway handle 60 is snapped off.

An axially extending stem 66 having a square cross section extends proximally from the housing 62. The stem 66 is inserted into an annular mount 68 whose proximal face is attached to the torque cable 19 and whose distal face is exposed to engage the housing 62.

The coupling between the torque cable 19 and the housing 62 can also be effected by, for example, providing a stem 66 having a circular cross-section. In this case, an adhesive or interference bond is applied between the stem 66 and the annular mount 68). Such a stem 66 can be provided with axial grooves to engage corresponding axial teeth circumferentially disposed in the interior wall of the annular mount 68. Stems with alternative cross sections can also be used to effect coupling. For example, a stem 66 having a semi-circular cross section can engage a corresponding semi-circular aperture in the annular mount 68. Or, the coupling can be affected by providing matching threads on the stem 66 and the annular mount 68, in which case the stem 66 can be screwed into the annular mount 68. In the case of a metal housing 62 and a metal annular mount 68, the housing 62 can be brazed, soldered, or welded directly to the annular mount 68. All the coupling methods described herein can be augmented by applying an adhesive at the engagement surfaces of the housing 62 and the annular mount 68.

Figure 6:
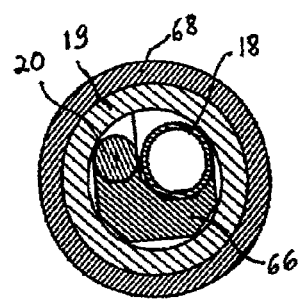
FIG. 6 is a cross-section through the torque cable proximate to the tip assembly of FIG. 3.

FIG. 6 is a cross-sectional view of the annular mount 68 sliced to reveal an upper portion that contains the collection and delivery fibers 18, 20 and a lower portion that accommodates the stem 66 extending from the housing 62.

The annular mount 68 can also have an optional marker groove 70 on its outer surface for accommodating a radio-opaque marker 72. An example of such an annular mount, shown in FIG. 5, has a marker groove 70 that aligns with a corresponding marker groove 71 on the housing 62.

The radio-opaque marker 72 can be a strip, as shown, a band, or any other convenient shape. The marker 72 can be any radio-opaque material such as gold, iridium, praseodymium, or platinum. Instead of, or in addition to the radio-opaque marker, either the housing 62 or the optical bench 42 (or both) can incorporate a radio-opaque material. For example, the plastic can be a compound plastic (such as polycarbonate, acrylonitrile butadiene styrene, or polyamide) with a powder from a radio-opaque material incorporated therein. Suitable radio-opaque materials include barium sulfate.

Figure 8:
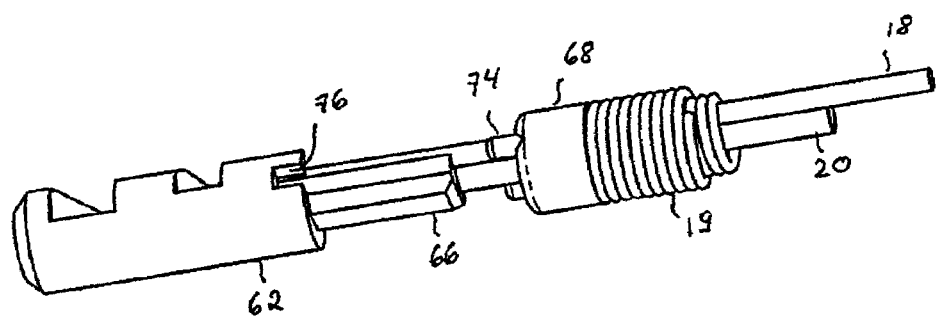
FIG. 8 is a housing having slots to receive tabs from a coupling mount attached to a torque cable.
Figure 7:
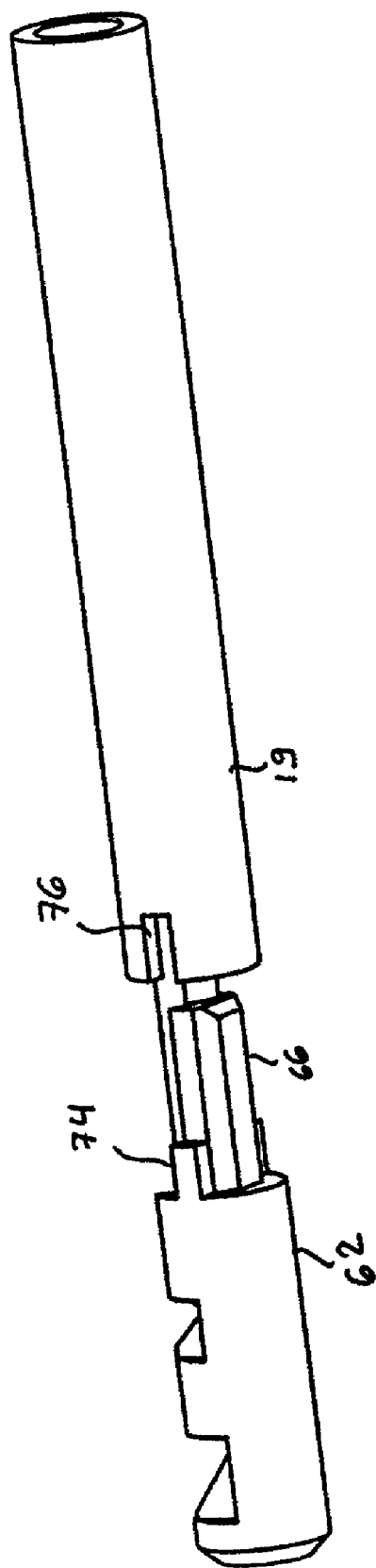
FIG. 7 is a housing having tabs for coupling to slots in a coupling mount attached to a torque cable.
Figure 9:
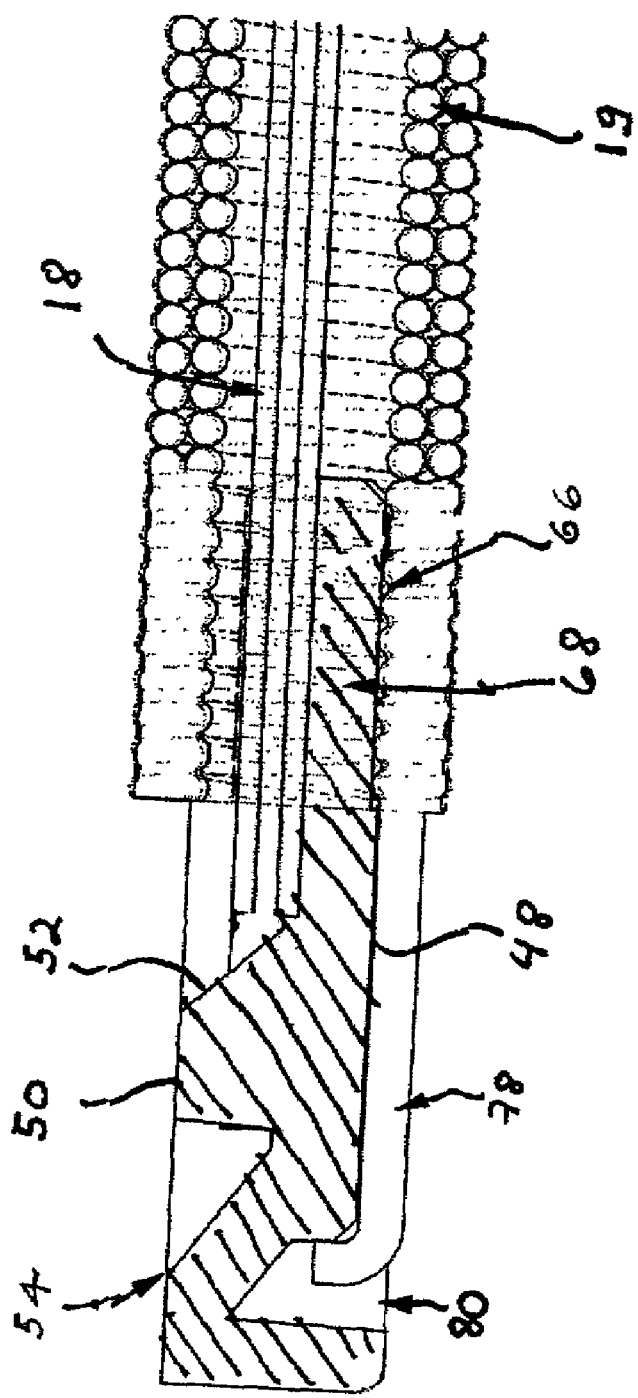
FIG. 9 is a housing coupled to a torque cable by a hook.
Figure 10:
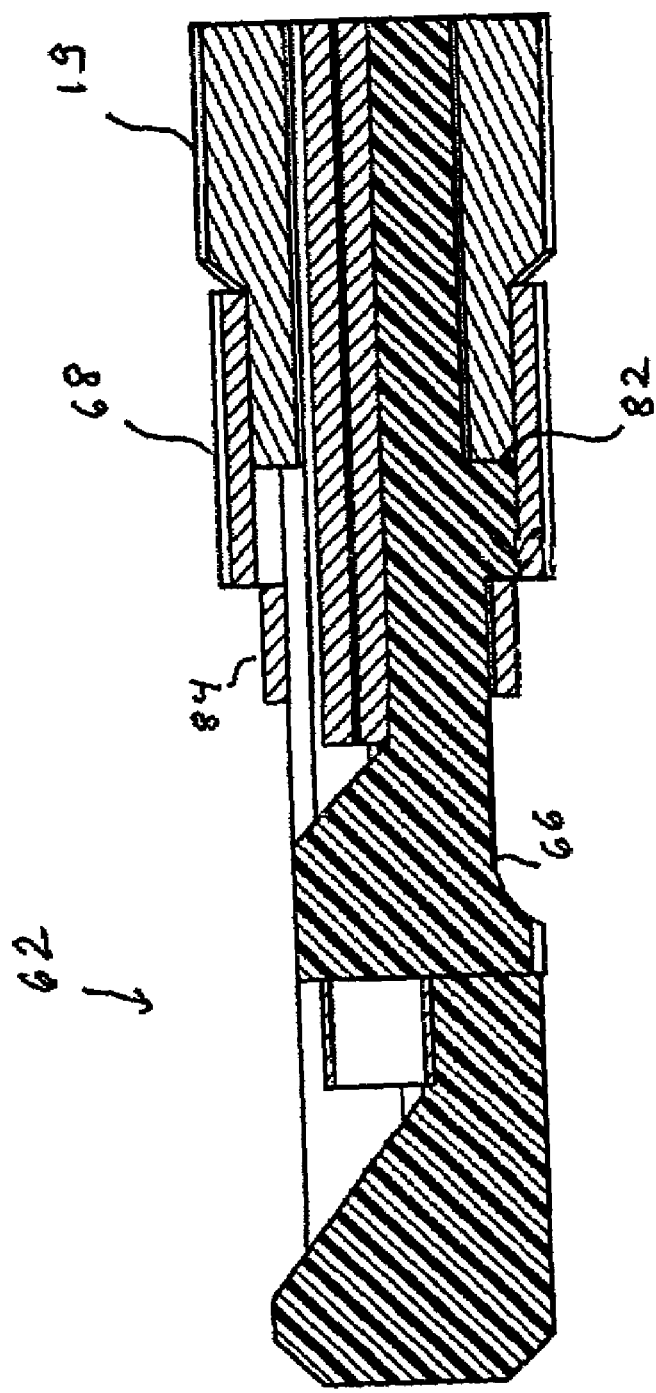
FIG. 10 is a housing coupled to the torque cable by a catch feature.

An alternative coupling structure, shown in FIG. 7, features a pair of axially extending tabs 74 protruding from the housing 62. These tabs 74 mate with a corresponding pair of axial slots 76 in the torque cable 19. The axially extending tabs 74 can instead protrude from the distal end of the annular mount 68, as shown in FIG. 8, and mate with corresponding axial slots 76 in the housing 62. FIG. 9 shows another coupling structure in which a hooked tab 78 extends proximally from the annular mount 68 and fits into a tab-receiving slot 80 on the housing 62. FIG. 10 shows yet another coupling structure in which a catch feature 82 is molded onto the stem 66. The stem 66 is inserted into the annular mount 68 until the catch feature 82 is completely inside. The distal end 84 of the annular mount 68 is then crimped, thereby securing the catch feature 82. Alternatively, the coupling shown in FIG. 10 can be effected by snapping the catch feature into place proximal to a reduced diameter distal end portion of the annular mount 68.

Using the Catheter

In use, the distal tip assembly 22 is inserted into a blood vessel, typically an artery, and guided to a location of interest. Light is then directed into the delivery fiber 18. This light exits the delivery fiber 18 at its distal tip, reflects off the delivery mirror 52 in a direction away from the plane containing the delivery and collection fibers 18, 20, and illuminates an illumination spot on the wall of the artery. Light penetrating the arterial wall 14 is then scattered by structures within the wall. Some of this scattered light re-enters the blood vessel and impinges on the plane and onto the collection mirror 54. The collection mirror 54 directs this light into the collection fiber 20.

Alternatively, light incident on the wall 14 can stimulate fluorescence from structures on or within the wall 14. The portion of this fluorescent light that is incident on the collection mirror 54 is directed into the collection fiber 20.

Figure 11:
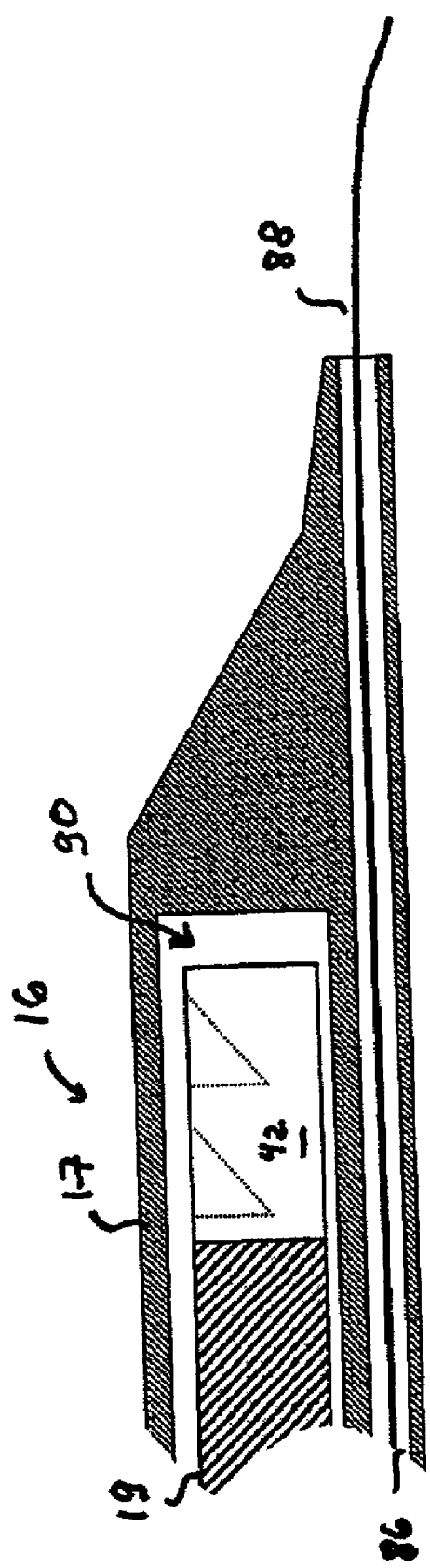
FIGS. 11-12 are cross-sections of a catheter sliding along a guide-wire.

The distal tip assembly 22 can be inserted into the blood vessel in a variety of ways. One method for inserting the distal tip assembly 22 is to provide a channel 86 that extends axially through the jacket 17 for accommodating a guide wire 88, as shown in FIG. 11. The guide-wire 88 is first inserted into the artery by itself and guided to the region of interest. Once the guide wire is in place, the guide wire is threaded through the channel 86. The jacket 17 is then slid along the guide-wire until its distal end reaches the region of interest. Then, the torque cable 19 with the distal tip assembly 22 at its distal end is inserted through a lumen 90 in the jacket 17.

Figure 12:
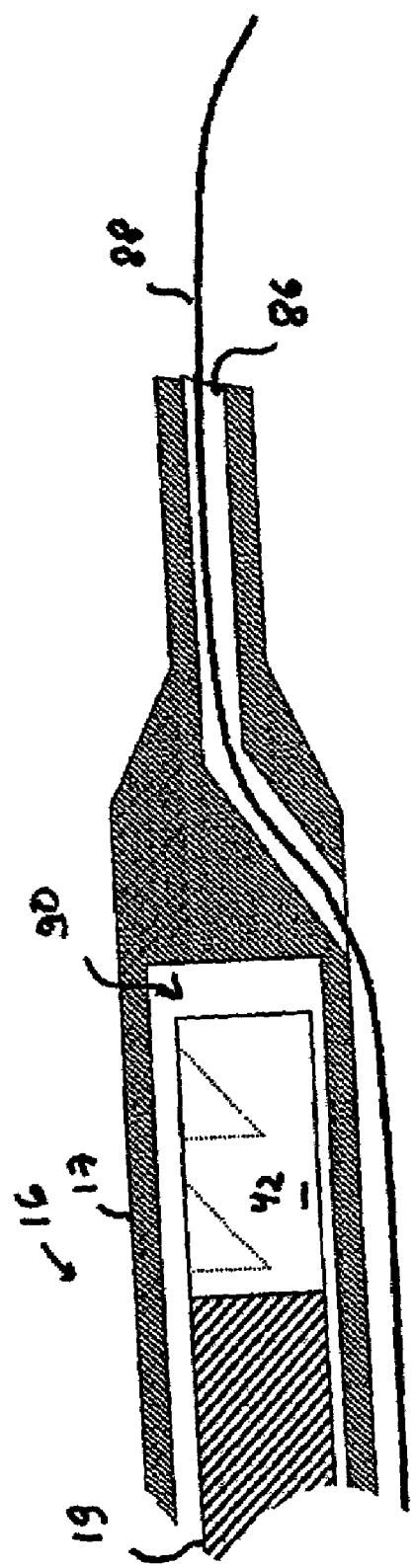

Alternatively, the jacket 17 can have a channel 86 extending only through a distal tip thereof, as shown in FIG. 12. The procedure for inserting the distal tip assembly 22 is identical to that described in connection with FIG. 11. However, this configuration provides a smaller transverse cross-section than that shown in FIG. 11, in which the channel 86 extends along the length of the jacket 17.

Figure 13:
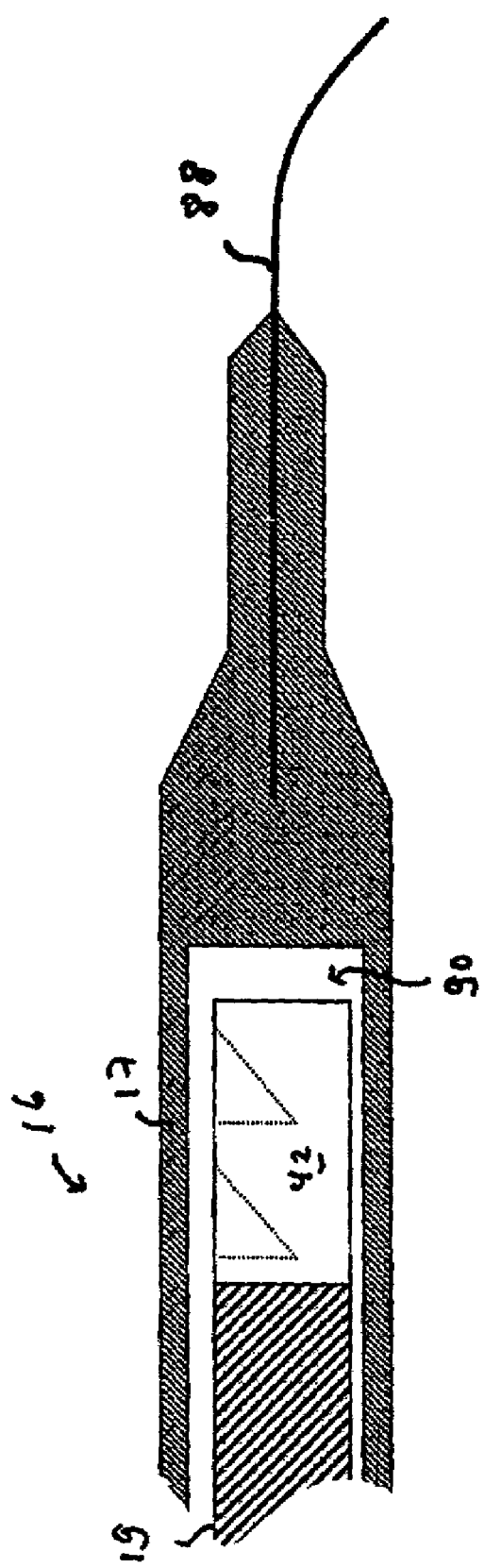
FIG. 13 is a cross-section of a guide wire mounted on a catheter.

An even smaller transverse configuration is provided by the configuration shown in FIG. 13, in which the channel is dispensed with altogether and the guide wire 88 is attached to, and extends from, the distal tip of the jacket 17. In this case, the jacket 17 is inserted into the artery and guided to the region of interest by using the guide wire 88 already attached to its tip.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A catheter tip assembly comprising:
   an optical bench extending along a longitudinal axis and having a transverse dimension selected to receive adjacent first and second fibers, the optical bench having first and second fixed beam re-directors in optical communication with respective first and second fibers, the first and second beam re-directors being oriented to cause respective first and second non-intersecting beams to travel away from the optical bench; and
   a housing having a recess for receiving the optical bench and an engaging structure for coupling to an end of a torque cable extending axially along a catheter, to provide a torque coupling between the housing and the torque cable.

2. The catheter tip assembly of claim 1, wherein the first beam redirector is selected from the group consisting of a mirror, a diffraction grating, and a prism.

3. The catheter tip assembly of claim 1, further comprising an optical fiber seated in the optical bench.

4. The catheter tip assembly of claim 3, wherein the first beam re-director comprises a distal end of the optical fiber.

5. The catheter tip assembly of claim 4, wherein the distal end of the optical fiber comprises a diagonal face oriented to direct a beam traveling through the fiber in a direction away from the fiber.

6. The catheter tip assembly of claim 1, further comprising a lens assembly disposed to provide optical communication between the first fiber and the first beam re-director.

7. The catheter tip assembly of claim 6, wherein the lens assembly comprises a GRIN lens.

8. The catheter tip assembly of claim 3, wherein the optical fiber comprises a lens integral with a distal end thereof.

9. The catheter tip assembly of claim 1, wherein the first beam re-director is oriented to cause a beam to travel in a direction perpendicular to the longitudinal axis.

10. The catheter tip assembly of claim 1, wherein the first and second beam re-directors are oriented to cause the first and second beams to travel in different directions.

11. The catheter tip assembly of claim 1, further comprising an annular coupling mount disposed between the torque cable and the housing, the annular coupling mount having a first face coupled to the torque cable and a second face for engaging the housing.

12. The catheter tip assembly of claim 11, wherein the housing comprises a proximally extending stem for inserting into an aperture in the annular coupling mount.

13. The catheter tip assembly of claim 11, wherein the housing comprises a tab extending proximally from a periphery thereof, and the annular coupling mount comprises a distal face having walls forming a slot for receiving the tab.

14. The catheter tip assembly of claim 11, wherein the annular coupling mount comprises a tab extending distally from a periphery thereof, and the housing comprises walls forming a slot for receiving the tab.

15. The catheter tip assembly of claim 11, wherein the annular coupling mount comprises a hook extending proximally into a recess in the housing.

16. The catheter tip assembly of claim 1, wherein the optical bench is manufactured by a process selected from the group consisting of injection molding, etching, micro-machining, silicon optical bench fabrication techniques, and photolithography.

17. The catheter tip assembly of claim 1, further comprising a radio-opaque marker fixed to the housing.

18. The catheter tip assembly of claim 1, wherein the first and second beam re-directors are oriented to cause parallel first and second beams to travel in a direction perpendicular to the longitudinal axis of the optical bench.

19. A catheter tip assembly comprising:
an optical bench having a recess extending along a longitudinal axis thereof, the recess having a transverse dimension selected to receive adjacent first and second fixed fibers, the optical bench having first and second fixed beam re-directors in optical communication with corresponding first and second fibers, the first and second beam re-directors being oriented to cause a pair of non-intersecting beams to travel away from the optical bench; and
an engaging structure for coupling to an end of a torque cable extending axially along a catheter, to provide a torque coupling between the optical bench and the torque cable.

20. The catheter tip assembly of claim 19, further comprising a housing, wherein the housing and the optical bench define a single unitary structure.

21. A catheter comprising:
a rotatable torque cable;
first and second optical fibers extending through the torque cable;
a catheter tip assembly having;
an optical bench extending along a longitudinal axis and having a transverse dimension selected to receive adjacent first and second fibers, the optical bench having first and second fixed beam re-directors in optical communication with respective first and second fibers, the first and second beam re-directors being oriented to cause respective first and second non-intersecting beams to travel away from the optical bench; and
a housing having a recess for receiving the optical bench and an engaging structure for coupling to an end of a torque cable extending axially along a catheter, to provide a torque coupling between the housing and the torque cable.

22. The catheter of claim 21, wherein the first and second beam re-directors are oriented to cause parallel first and second beams to travel in a direction perpendicular to the longitudinal axis of the optical bench.

23. The catheter of claim 21, wherein the first beam re-director is oriented to cause a beam to travel in a direction perpendicular to the longitudinal axis.

24. The catheter of claim 21, wherein the first and second beam re-directors are oriented to cause the first and second beams to travel in different directions.

25. The catheter of claim 21, further comprising an annular coupling mount disposed between the torque cable and the housing, the annular coupling mount having a first face coupled to the torque cable and a second face for engaging the housing.

26. The catheter of claim 25, wherein the housing comprises a proximally extending stem for inserting into an aperture in the annular coupling mount.

27. The catheter of claim 25, wherein the housing comprises a tab extending proximally from a periphery thereof, and the annular coupling mount comprises a distal face having walls forming a slot for receiving the tab.

28. The catheter of claim 25, wherein the annular coupling mount comprises a tab extending distally from a periphery thereof, and the housing comprises walls forming a slot for receiving the tab.

29. The catheter of claim 25, wherein the annular coupling mount comprises a hook extending proximally into a recess in the housing.

30. A catheter tip assembly comprising:
an optical bench extending along a longitudinal axis and having a transverse dimension selected to receive adjacent first and second fibers, the optical bench having first and second fixed beam re-directors in optical communication with respective first and second fibers, the first and second beam re-directors being oriented to cause respective first and second non-intersecting beams to travel away from the optical bench; and
a housing integral with the optical bench and an engaging structure for coupling to an end of a torque cable extending axially along a catheter, to provide a torque coupling between the housing and the torque cable.

31. A catheter comprising:
a rotatable torque cable;
first and second optical fibers extending through the torque cable;
a catheter tip assembly having
an optical bench extending along a longitudinal axis and having a transverse dimension selected to receive adjacent first and second fibers, the optical bench having first and second fixed beam re-directors in optical communication with respective first and second fibers, the first and second beam re-directors being oriented to cause respective first and second non-intersecting beams to travel away from the optical bench; and
a housing integral with the optical bench and an engaging structure for coupling to an end of a torque cable extending axially along a catheter, to provide a torque coupling between the housing and the torque cable.

* * * * *